United States Patent [19]

Monti et al.

[11] Patent Number: 4,617,691
[45] Date of Patent: Oct. 21, 1986

[54] SUPPORT PILLOW

[76] Inventors: Martha S. Monti; Gilbert L. Monti, both of P.O. Box 9428, Phoenix, Ariz. 85068

[21] Appl. No.: 746,451

[22] Filed: Jun. 19, 1985

Related U.S. Application Data

[63] Continuation of Ser. No. 487,989, Apr. 25, 1983, abandoned.

[51] Int. Cl.$^4$ ............................ A47G 9/00; A61H 1/02
[52] U.S. Cl. ............................................ 5/434; 5/436; 5/437; 5/439; 128/DIG. 23
[58] Field of Search ...................... 5/434–436, 5/441, 442, 443; 297/393, 391; 128/68, DIG. 23; D6/601, 604

[56] References Cited

U.S. PATENT DOCUMENTS

| 941,043 | 11/1909 | Powell | 5/436 |
|---|---|---|---|
| 2,336,707 | 12/1943 | Thompson | 5/436 |
| 3,164,151 | 1/1965 | Nicoll | 128/DIG. 23 |
| 4,232,663 | 4/1980 | Newton | 128/DIG. 23 |
| 4,236,264 | 12/1980 | Britzman | 5/435 |

FOREIGN PATENT DOCUMENTS

| 8102384 | 9/1981 | PCT Int'l Appl. | 5/464 |
|---|---|---|---|
| 838455 | 6/1960 | United Kingdom | 297/393 |

Primary Examiner—Alexander Grosz
Attorney, Agent, or Firm—Harry M. Weiss & Associates

[57] ABSTRACT

A generally rectangular or other suitably shaped support pillow adapted to be removably secured around a users neck. A single elongated wedge-shaped pillow segment is provided with fasteners for joining one end to the other. The wedge shape gives increased lateral support to the users neck and head. Worn with the fasteners under the user's chin, it gives increased head and neck support whereas if it is worn with the fasteners behind the users head, it gives increased chin and head support. A three piece version is also provided and the various pillow segments may be of various sizes. A laminate may be applied to render the support pillow bacteria proof, flame retardent and waterproof while allowing heat and perspiration to escape. A spring-like closure version is also shown.

1 Claim, 13 Drawing Figures

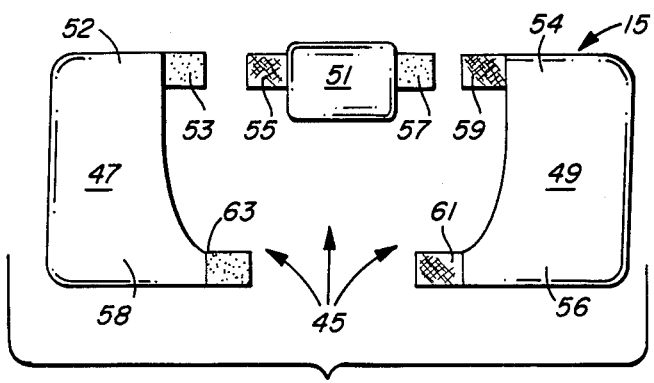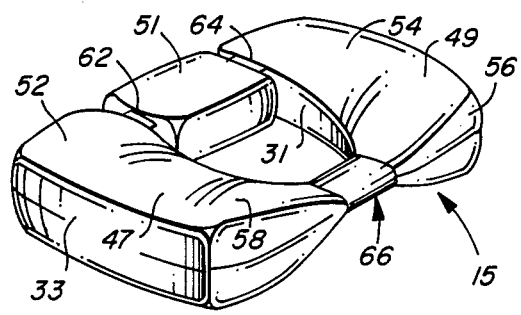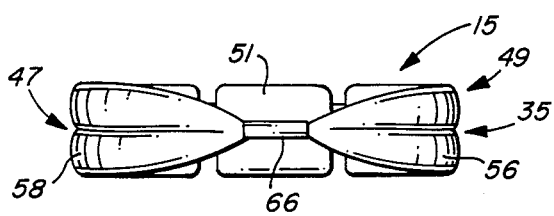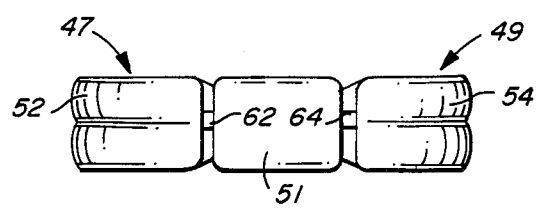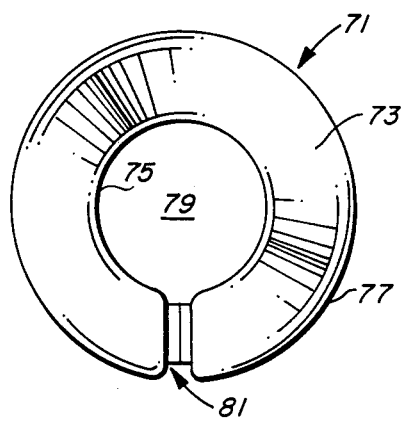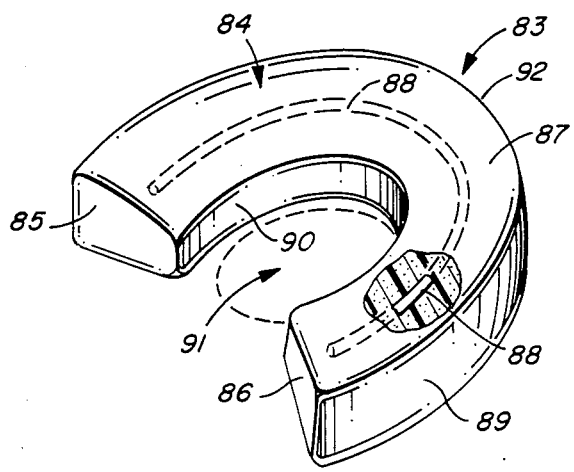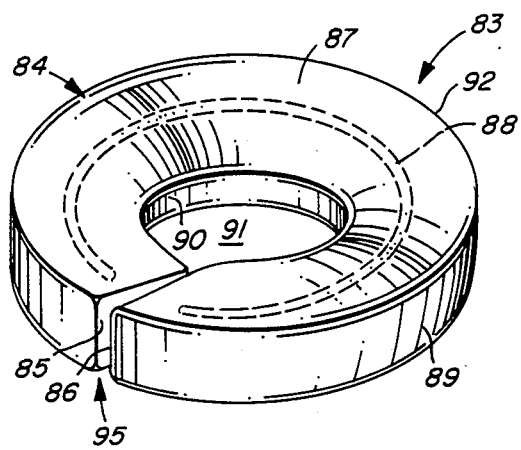

SUPPORT PILLOW

This application is a continuation of application Ser. No. 487,989, filed Apr. 25, 1983, now abandoned.

BACKGROUND OF THE INVNETION

1. Field of the Invention

This invention relates generally to a head and neck support pillow and more particularly to a support pillow not of the medical type for primary restriction such as surgical collars and the like but which can serve a multiple of mild support purposes including providing improved lateral head and neck support, providing chin and head support, and/or providing improved support to the back of the neck.

2. Description of the Prior Art

For years infants, toddlers, and small children sitting or riding in car seats, carriers, walkers, strollers, swings, jumpers, high chairs, and similar seat-like devices have been rudely awakened when their heads fell forward, backward, or sideways as they drifted off to sleep or due to bumps or acceleration variations in the ride. Such infants, toddlers, and children were not only rudely awakened, but, in many instances, suffered injuries which resulted in at least prolonged crying or the like.

More seriously, modern doctors realize the importance of protecting a child's delicate neck and head from twisting, turning, sudden shifts in direction, and of course contusions and the like. These children can not be routinely provided with any type of restrictive surgical brace or collar so the standard prior art solution was to place a common pillow behind the child's head. This, of course, left the sides of the neck and head and front exposed unless the person protecting the child decided to stuff four separate pillows or a blanket or the like around the baby for protection purposes. This, of course, overheated the baby or child making it extremely uncomfortable and difficult to sleep, and often squeezed it into the seat adding still additional discomfort. Bib-like devices or simplistic collars of the prior art offered no real solution to these problems.

The travel industry is also an important source of support pillow useage. Air travel, trains, busses, subways and other forms of mass transportation illustrate the need for support pillows for older children and adults as well as infants, toddlers, and small children, regardless of the particular type of seat used. As increased amounts of time are spent on airplanes, trains, busses, automobiles and the like, the carrier must plan on offering the traveler an opportunity to rest up or sleep in preparation for arrival at his destination or at least see that he rests comfortably during the trip. However, most types of mass transportation require that any resting or sleep which the traveler gets he must get in a seated or substantially vertical position. Sleeping in this position often permits the head to bob and/or twist, turn or rest for long periods of time in an unnatural position. This results in lack of sleep or rest and often in a cramped neck, sore muscles or the like. The prior art recognized the need to provide some type of light support to the head and neck area so as to permit more comfortable rest during travel and resolved the problem by using standard type pillows and rolled up blankets which have proved wholly unsatisfactory. These standard pillows, and more often than not, substandard pillows, offered little or no support and provided a simple head rest at best at either the back of the head or the back of the neck but seldom both. Furthermore, the covers to these pillows were often dirty and unsanitary, absorbed sweat and moisture from the travelers head and neck area and smelled.

Another area in the prior art recognizing the need for support pillows is the medical area. While the medical area is replete with braces and the like to provide primary restriction, such devices are not useable to provide simple light support and comfort for its users, particularly small children and the like. Further, the medical area has recognized the need for a support device to discourage a user, often a medical patient, from rolling out of a predetermined position while sleeping in a horizontal position. Surgical pillows provide excellent support to the back of the neck while sleeping in a horizontal position but they offer little or no restriction to keep the person from physically rolling out of the desired position or even out of bed.

Further, the prior art teaches the need for a light comfortable support apparatus for use when a primary restrictive apparatus such as a surgical collar for the neck and head was not presently being worn or was not required. For example, patients having difficulty with muscle control of the neck or patients bound to wheelchairs often require or desire some form of neck support even during periods when rigid braces or collars which were used as primary restrictive devices were removed. There was no apparatus available for use when the primary restrictive apparatus is temporarily removed and thus those patients who require secondary or relatively mild support during the interum periods, remain wanting. Therefore, a need still exists in the prior art for a relatively mild or comfortable support pillow or apparatus which is capable of providing less than true restrictive support to the head and neck area of a person and thus provide comfort and/or medical benefits to that person.

Furthermore, the need exists for a relatively simple, light weight, washable, medically acceptable, head and neck support capable of providing various types of support for comfort and protection. Yet further, a need exists for a support pillow which permits restful sleep for the user in the vertical position, which provides improved support to discourage the user from rolling out of the desired position when used during periods of horizontal rest, and which provides improved support as a supplement to primary restrictive apparatus during periods of non-use. Lastly, the prior art teaches the need for a support pillow which offers head and neck support and substantial protection to infants, toddlers, and small children in various seat-like devices; and which can be rendered fire proof, water proof, moisture proof, bacteria proof, while being able to breath to eliminate evaporation and perspiration; able to pass heat to prevent rashes and the like; and which may be quickly and easily assembled and/or put on and taken off a user's neck.

The support pillow of the present invention solves substantially all of these problems and provides a relatively low cost, extremely simple means whereby a user can receive head and neck support of various types depending upon the positioning of the pillow.

SUMMARY OF THE INVENTION

The present invention provides a support pillow having a geometric shape adapted to be disposed substantially around the user's neck and at least partially carried on his shoulders. The pillow includes at least one elongated pillow segment and adjustably positionable fastening tabs for securing the pillow segment longitudinally to substantially encircle the user's neck. The fastening means is of sufficient length for to allow adjustment to provide for an individual user's comfort and to provide a tighter fit, if required for added support.

In the preferred embodiment, the pillow segment is laterally wedge-shape and radially positioned with the wider wedge-shaped portion disposed away from the user's neck to give greater lateral head and neck support. While the present invention contemplates that the fastening means secures the pillow segment about the user's neck to form a rectangle, a pillow of any conventional shape such as a polygon, square, triangle, circle, oval or the like may also be used with the present invention, at least for various aspects thereof.

The preferred embodiment also contemplates that the pillow segments are stuffed or filled with a non-allergetic fill material and that the pillow be covered or coated with a laminated membrane, such as GORE-TEX ® (this is a registered trademark which describes a waterproofing material that has TEFLON ®, which is a registered trademark, material laminated with other material), at least for medical purposes, which render the pillow segments heat resistant, water proof, impervious to bacteria, and include breathability for allowing perspiration and evaporation therethrough and for dissipating heat to the atmosphere to prevent overheating, rashes and the like.

Yet further, an additional embodiment includes a three-part pillow segment support pillow wherein each of two elongated sides are connected to one another in the rear via a third pillow segment and the front of the first and second elongated pillows includes fastener means for securing the pillow about the user's neck as previously described. Various thicknesses and different sizes of pillows and pillow segments may be provided depending upon medical reasons, if applicable. Other advantages and meritorious features of the present invention will be more fully understood from the following description of the drawings and the preferred embodiments, the appended claims and the drawings which are described hereinbelow.

BRIEF DESCRIPTION OF THE DRAWINGS

FIG. 7 is an exploded top view of the three piece embodiment of the support pillow of the present invention;

FIG. 8 is a perspective view of the three piece support pillow of FIG. 7 in the assembled position;

FIG. 9 is a front view of the three piece support pillow of FIG. 8;

FIG. 10 is a rear view of the three piece support pillow of FIG. 8;

FIG. 11 is an alternate embodiment showing a top view including a generally circular support pillow;

FIG. 12 is a perspective view, partly broken away, of an alternate embodiment including a spring means for opening the ends of the pillow segment for application about the user's neck; and FIG. 13 is a perspective view of the pillow of FIG. 12 returned to its normal position for closing the pillow about the user's neck in a general oval shape.

DESCRIPTION OF THE PREFERRED EMBODIMENT

Figure 1:
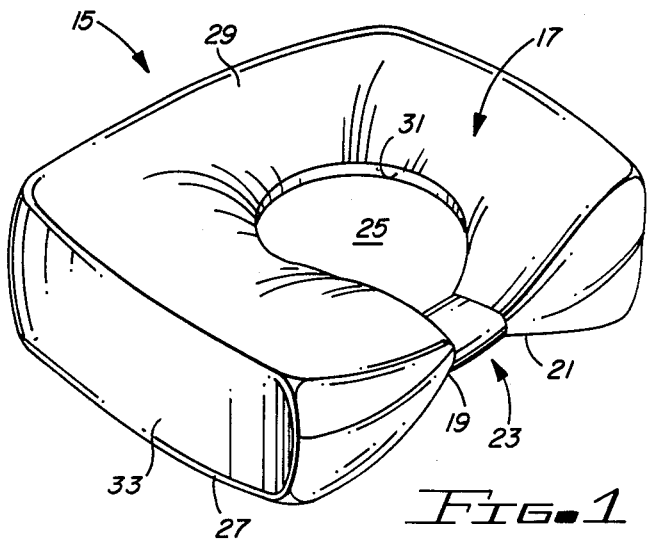
FIG. 1 is a perspective view of the preferred embodiment of the support pillow of the present invention.

FIG. 1 is a perspective view of the preferred embodiment of the support pillow 15 of the present invention. The support pillow 15 includes a single elongated body or pillow segment 17 having one end 19 detachably secured to the opposite end 21 through the use of a quick action attach-detach member 23. Once the ends 19, 21 of the pillow segment 17 are attached together, the elongated segment 17 takes on a generally rectangular shape with a generally circular or oval aperture 25 in the middle thereof for removably receiving a person's neck. The bottom 27 of the pillow segment 17 is adapted to rest or be positioned on the user's shoulder and the rear portion 29 is relatively thick compared to the central front portion where the fastening means 23 is attached. The terms back and front are used for describing the figures only and it will be understood that the pillow can be rotated on the user's head or installed in the opposite direction so that back and front are reversed with respect to the user's face, as hereinafter described.

The inside surface or edge portion 31 of the pillow segment 17 is adapted to be comfortably positioned against the user's neck and is, in the preferred embodiment of the present invention, relatively thin in its top to bottom dimension. The outside 33, however, is relatively thick compared to the thickness of the inside portion 31 so as to form a laterally wedge-shaped elongated member 17 which provides increased lateral support to the user's head and neck. In the preferred embodiment of FIG. 1, it is understood that the actual size, shape and dimensions of the support pillow 15 may be varied depending upon whether or not the support pillow is for an infant, a child or an adult. Likewise, the shape may be changed for medical reasons as hereinafter described. Further, the rectangular shape may be polygonal, square, triangular, circular, oval, or the like provided the dimensions are such that the objects of the present invention are still met.

The inside of the elongated pillow segment 17 is stuffed or filled with a conventional non-allergenic fill material. For at least some applications, including medical use, the material of the support pillow 15 can be sprayed or covered to laminate it with a unique membrane such as GORE-TEX ®. The addition of this laminated membrane renders the pillow 15 flame retardant, waterproof, bacteria proof so bacteria cannot penetrate the membrane and establish an internal breeding ground, breathable to allow perspiration to evaporate and heat to dissipate so as to prevent heat rash and the like thereby making the pillow 15 comfortable to wear. Being waterproof, any bodily discharge will not be absorbed by the pillow segment 17 but can be easily wiped off to keep the pillow 15 clean at all times.

Figure 2:
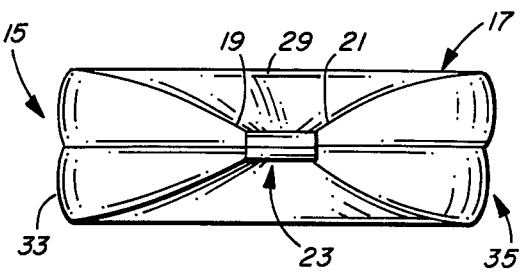
FIG. 2 is a front view of the support pillow of FIG. 1.

FIG. 2 is a front view of the support pillow 15 of FIG. 1 and it further illustrates the thicker rear portion 29, the ends 19 and 21 of the elongated segment 17, the fastener 23 connecting the ends 19 and 21 and the relatively thick lateral sides 33 of the pillow segment 17 which form the general wedge-shaped configuration 35 which slopes from the outer edge 33 into the area encircling the user's neck.

Figure 3:
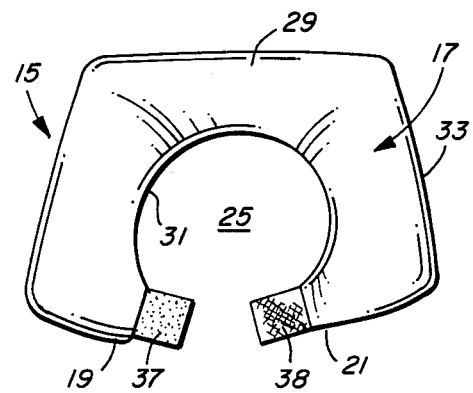
FIG. 3 is a top view of the support pillow of FIG. 2 with the fasteners in the opened position.

FIG. 3 is a top view of the support pillow of FIG. 1 with the fasteners 23 opened to separate the ends 19, 21 of the tubular pillow segment 17 for putting it on or taking it off of the user's neck. The interior cavity or opening 25 is opened further than usual to receive or allow removal of the neck and the inside surface 31 may be temporarily out of contact or proximate contact therewith. The outer surfaces 33 are spread while the back portion 29 remains substantially the same. The fastening device 23 is shown as including a pair of conventional VELCRO ® (this is a registered trademark and describes a hook and loop fastening mechanism or material) fastener tabs 37, 38 with tab 37 secured to end 19 and tab 38 secured to end 21. As conventionally known, one of the tabs 37, 38 contains the hook members while the other contains the latching pad or loops so that when the tabs 37, 38 are overlayed on top of one another and selectively adjusted to provide the correct degree of tightness while still providing for user comfort, they are pressed together to secure the ends 19, 21 thereby positioning the pillow segment 17 around the user's neck restoring it to its generally rectangular shape.

Figure 4:
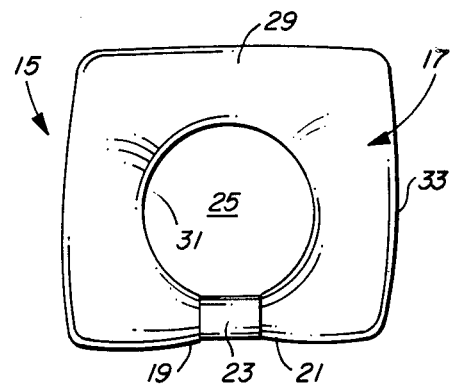
FIG. 4 is a top view of the support pillow of FIG. 2 with the fasteners in the closed position.

FIG. 4 is a top view of the support pillow 15 of FIG. 3 and illustrates the elongated pillow segment 17 in the closed position so as to form a generally circular or oval aperture 25 for receiving the user's neck in the center thereof, with the inside edge surface 31 in proximate contact to the user's neck, and the outer edge 33 being substantially thicker to provide the wedge-shape of the pillow for lateral support. The back 29 is shown as generally opposite the front portion having end 19 and end 21 removably secured by the fastening tabs 23.

Figure 5:
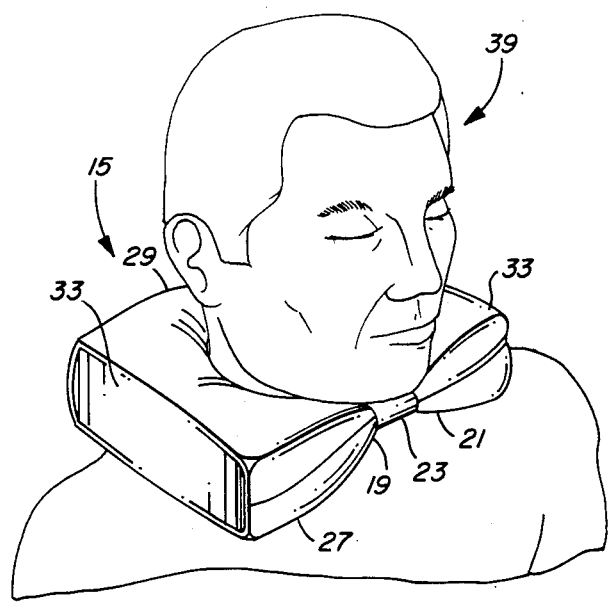
FIG. 5 is a perspective view illustrating the support pillow of the present invention worn about a user's neck with the fastening means under the user's chin.
Figure 6:
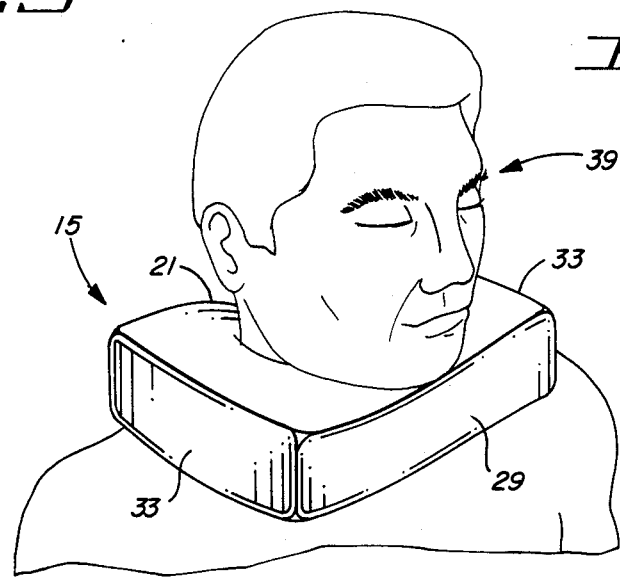
FIG. 6 is a perspective view of the support pillow of the present invention with the rear portion of the support pillow operably disposed beneath the user's chin.

FIG. 5 illustrates the use of the support pillow 15 of the present invention on a user 39. The bottom surface 27 rests generally on the user's shoulder while the wedge-shape 35 produced from the outer edge 33 to the portion 31 adjacent the user's neck provides increased lateral support. Further, since the generally thick back portion 29 of FIG. 1 is positioned behind the user's 39 head while the fastener 23 connects the ends 19, 21 and is disposed generally under the user's chin, the support pillow 15 provides the following advantages in this position. Firstly, it provides increased lateral support due to the wedge-shaped configuration thereof and secondly, when it is worn with the fastening tabs 23 in the front, the back portion 29 will give added support to the back of the neck. As shown in FIG. 6, when the relatively thick back portion 29 is disposed adjacent to or under the chin of the user 39, so that the ends 19, 21 and fastener 23 of FIG. 1 are disposed behind the user's head, the support pillow 15 offers a different set of advantages. Firstly, it still provides improved lateral support due to the relative thickness of sides 33 compared to the thickness of the sides 31 adjacent the user's neck. Secondly, with the fastening tab worn in the back, the thicker back cushion portion 29 will give additional support under the chin to keep the user's head from falling forward.

FIG. 7 shows a separated view of the three piece support pillow 15 of an alternate embodiment of the present invention. In FIG. 7, a first elongated side pillow portion or member 47, a second elongated side pillow portion or member 49 and a small pillow portion 51. Each of the pillow portions 47, 49 and 51 has a pair of VELCRO ® pads so that it can be detachably connected to form a generally rectangular support pillow 15. The rear tab 53 at the back end 52 of pillow segment 47 is detachably connected to tab 55 at one end of the small pillow 51. The tab 57 at the opposite end of the small pillow 51 is detachably connected to a tab 59 at the rear end 54 of the elongated side pillow portion 49. The front 56 of side pillow portion 49 and the front 58 of side pillow portion 47 are connected together by tabs 61 and 63 for forming a generally rectangular support pillow 15 from three individual pillow pieces.

The FIG. 8 is a perspective view of the three piece pillow support 15 of FIG. 7 connected together to form a support pillow 15. The first side pillow member 47 has its rear end 52 connected via fasteners 62 including the tabs 53 and 55 to one end of the small pillow 51. The opposite end of the pillow 51 is connected to the rear end of the elongated side pillow member 49 by fastener 64 comprising tabs 57 and 59. The front portion 56 of side pillow portion 49 and the front portion 58 of side pillow portion 47 are connected together by fasteners 66 comprising tabs 61 and 63 for forming a three piece support pillow 15. The inside surface 31 of the pillow 15 or at least the pillow portions 47 and 49 are adapted to be operably disposed adjacent or against the user's neck and the general shape of at least the first pillow portion 47 and second pillow portion 49 is wedge-shaped to provide lateral support. The shape of the small pillow 51 is not as critical but may also be wedge-shaped. It will, of course, be understood that each of the pillow segments or portions 47, 51 and 49 may be of a different size, thickness or shape for particular uses, such as medical needs or the like.

FIG. 9 is a front view of the three piece support pillow 15 of FIG. 8 illustrating the left side pillow portion 47, the rear pillow 51, the right side pillow portion 49, the front 56 of pillow portion 49, the front 58 of pillow portion 47, and the fastener device 66 connecting the ends 58 and 56 to form the generally rectangular support pillow of the present invention. Furthermore, the sides 35 are generally wedge-shaped for added lateral support.

FIG. 10 is a rear view of the perspective view of the three piece support pillow 15 of FIG. 8 showing the rear surface 52 of left pillow portion 47, the rear surface 54 of right pillow portion 49, the fastening device 64 including the tabs 57 and 59 which connect one end 54 of pillow portion 49 to one end of pillow 51 and a second fastening device 62 including tabs 53 and 55 which connect the opposite end 52 of the elongated pillow segment 47 to the small pillow 51 at the other end thereof.

FIG. 11 shows a generally circular support pillow 71 having a generally circular or oval inner surface 75, having a first thickness, a single elongated pillow portion 73, a generally thicker outer portion 77 of the elongated pillow 73 for providing a generally wedge-shape between the outer surface 77 and the inner surface 75 for increased lateral support. The support pillow 71 of FIG. 11 also includes fastener means 81 for securing one end of the elongated pillow segment 73 to the other for operational use.

FIG. 12 is another alternate embodiment of the support pillow 83 of the present invention. The support pillow 83 includes a single elongated pillow segment 84 having a first end 85 and a second end 86. An outer surface 89 is sufficiently thicker than the inner circular collar portion 90 to provide a wedge-shape to increase lateral support, as previously described. The interior or inside of the elongated pillow segment 84 is stuffed or filled with a fill material or the like, and, in the preferred embodiment of the present invention, a non-allergenic film material or laminate is used to cover the pillow surface. Retainably disposed within the fill material 87 is a U-clamp or spring 88. The clamp or spring 88 may include spring metal, resilient plastic, or some similar type of conventional spring-type material. The rear 92 of the elongated pillow portion 84 is preferably thicker than the area adjacent the ends 85, 86 to establish a front and back and FIG. 12 shows the front ends 85, 86 as they have been manually separated by pulling outward against the bias of the U-shaped spring 88 to allow the pillow 83 to be put on or taken off a user's neck 91.

FIG. 13 shows the pillow support 83 of FIG. 12 in the closed position with the user's neck 91 within the inner surface 90. After the user has placed and opened support pillow 83 of FIG. 12 around his neck 91, he slowly releases the ends 85, 86 allowing the spring 88 to return to its normally-biased position which closes the ends 85, 86 upon one another at 95. As with the support pillow 15 of FIG. 1, the support pillow 83 of FIGS. 12 and 13 provide a lateral support at all times and additionally, whenever the portion 95 is worn in the front adjacent the user's neck 91, the thicker rear cushion portion 92 will give increased support to the back of the neck and when the end portion 95 is worn adjacent the back of the neck, the thicker portion 92 is operably disposed beneath and against the user's chin to prevent his head from falling forward and the like. Further, VELCRO ® fastener pads could be applied to ends 85, 86 for detachably securing the ends 85, 86 together after the spring 88 has closed them upon one another.

With any of the embodiments described herein and particularly for those which find medical use, the support pillow may be sprayed, covered, or laminated with a unique membrane material such as GORE-TEX ®. This membrane renders the support pillow waterproof, fire retardent, bacteria proof, breathable to allow perspiration to escape and evaporate and heat conductive to allow heat to escape and dissipate thus making the pillow more comfortable to wear. Furthermore, being waterproof allows any bodily discharges to be easily wiped off rather than absorbed by the pillow. While various suitable types of fasteners may be used, the present invention contemplates conventional VELCRO ® tabs which can be of suffcient length to be adjustable for user comfort. The VELCRO ® tabs also allow the support pillow to be placed in a position of minimal movement and allows placement on person's who are sleeping without disturbing them. Furthermore, the tabs make possible a tighter fit around the neck for greater comfort and support, if desired.

Similarly, the pillows 15 may be provided in varying thicknesses and sizes and the wedge-shaped portions may have the outside to inside ratios changed, as desired. The support pillow 15 of the present invention may be laundered by conventional means, dry-cleaned or cleaned under hospital-like sterilization processes. Furthermore, the material may come in various colors and designs making the pillow more cheerful and attractive to the user. Some pillows may be manufactured with unisex preference materials while others are manufactured with male preference materials, female preference materials, children preference materials, and infants preference materials.

The support pillow 15 described herein is not designed to immobilize head movement like a surgical collar or for any other type of medical requirement employing a tight restriction, but rather as a comfortable support for a head and neck to be used while sleeping or resting in a seated or vertical position. Furthermore, the support pillow can be used for a horizontal rest. This application gives excellent support to the back of the neck as does a surgical pillow. However, unlike a surgical pillow, the pillow 15 of the present invention discourages the user from rolling out of position due to its shape, the encircling effect, and the fasteners. The pillow 15 has proved ideal for children riding in carseats or any other type of seats and particulary effective at allowing children to sleep safely and peacefully by eliminating irritating head bobbing. Adults as well may use the pillow for getting rest while they travel and it can even be provided with a travel case for convenience of storage and for keeping it clean when not in use. The pillow 15 covers can, as known in the art, be made removeable, if desired, for cleaning purposes or cover changes to different colors etc.

Commercial air carriers, trains, busses, subways and the like may find the present invention a substitute for individual cloth pillows with throw-away covers and inherent sweat absorption and smell problems. The present pillow 15 may also have many medical applications. For example, a patient having difficult with muscle control of the neck and simply as a comfort item to patients bound to wheelchairs. While the pillow 15 is not designed as a primary restrictive apparatus but rather as a supplement to be worn for comfort and support during those periods when the primary apparatus is not worn, or as an item to fill the void where such apparatus is not necessary and only light support is required. The support pillow of the present invention is being tested by several doctors and is approved by all those who have completed their testing.

With this detailed description of the specific apparatus used to illustrate the present invention and the operation thereof, it will be obvious to those skilled in the art that various modifications can be made without departing from the spirit and scope of the present invention which is limited only by the appended claims.

We claim:

1. A pillow adapted to encircle a user's neck while resting on the user's shoulders, said pillow comprising an elongated segment with a substantially homogeneous filling forming a pillow of generally rectangular shape in top plan view, with a circular opening therein, and including an inner vertical surface having a first generally constant thickness, for fitting substantially around the user's neck and an outer peripheral vertical edge surface having a second generally constant thickness, said outer peripheral edge surface being spaced substantially laterally apart from said inner surface and said second thickness being substantially greater than said first thickness for providing a wedge shaped support pillow that provides improved lateral support around the user's neck and head; and tear fastener means located at the end portions of the elongated segment forming said pillow, said fastener means adapted to selectively adjust the fastened positions to insure user comfort and adapted to produce a tighter fit if greater head support is desired, said pillow providing increased support for the back of user's neck whenever said tear fastener means is positioned in front of the user and under his chin and said pillow providing increased support for the user's chin and head whenever said tear fastener means is positioned in the back of the user's neck.

* * * * *